United States Patent
Ren et al.

(10) Patent No.: US 11,542,244 B2
(45) Date of Patent: Jan. 3, 2023

(54) SYNTHESIS OF TIPIFARNIB

(71) Applicant: KURA ONCOLOGY, INC., San Diego, CA (US)

(72) Inventors: Pingda Ren, San Diego, CA (US); Xiaohu Deng, San Diego, CA (US); Wanping Mai, San Diego, CA (US)

(73) Assignee: KURA ONCOLOGY, INC., San Diego, CA (US)

( * ) Notice: Subject to any disclaimer, the term of this patent is extended or adjusted under 35 U.S.C. 154(b) by 0 days.

(21) Appl. No.: 17/056,745

(22) PCT Filed: May 17, 2019

(86) PCT No.: PCT/US2019/032765
§ 371 (c)(1),
(2) Date: Nov. 18, 2020

(87) PCT Pub. No.: WO2019/222565
PCT Pub. Date: Nov. 21, 2019

(65) Prior Publication Data
US 2021/0246114 A1 Aug. 12, 2021

Related U.S. Application Data

(60) Provisional application No. 62/673,693, filed on May 18, 2018.

(51) Int. Cl.
*C07D 401/06* (2006.01)

(52) U.S. Cl.
CPC ........ *C07D 401/06* (2013.01); *C07B 2200/07* (2013.01); *C07B 2200/13* (2013.01)

(58) Field of Classification Search
CPC ........ C07D 401/06; C07B 55/00; C07B 57/00
USPC .......................................................... 546/157
See application file for complete search history.

(56) References Cited

U.S. PATENT DOCUMENTS

| | | | |
|---|---|---|---|
| 7,456,287 B2 * | 11/2008 | Filliers | A61P 43/00 546/157 |
| 7,524,961 B2 * | 4/2009 | Filliers | C07D 215/227 546/168 |

FOREIGN PATENT DOCUMENTS

| | | |
|---|---|---|
| CN | 104876856 A | 9/2015 |
| EP | 0 768 309 A1 | 4/1997 |
| WO | WO 1996/09290 A1 | 3/1996 |
| WO | WO 2002/072574 A1 | 9/2002 |
| WO | WO 2005/105784 A1 | 4/2005 |
| WO | WO 2005/105783 A1 | 11/2005 |
| WO | WO 2016/078758 A1 | 5/2016 |

OTHER PUBLICATIONS

Vaidya N.A. (2006) "Diastereomeric crystallizatio—the "classical" chiral technology," Journal of Chemical Technology, 82-85. Available at: https://web.archive.org/web/20061022020816/http://iptonline.com/articles/public/IPTNINE82NoPrint.pdf.

* cited by examiner

*Primary Examiner* — Charanjit Aulakh
(74) *Attorney, Agent, or Firm* — Jones Day

(57) ABSTRACT

Provided herein are methods of preparing a desired enantiomer 6-[amino(4-chlorophenyl)(1-methyl-1H-imidazol-5-yl) methyl]-4-(3-chlorophenyl)-1-methyl-2(1H)-quinolinone, otherwise known as tipifarnib.

29 Claims, No Drawings

SYNTHESIS OF TIPIFARNIB

CROSS-REFERENCE TO RELATED APPLICATIONS

This application is a U.S. national stage of International Patent Application No. PCT/US2019/032765, filed May 17, 2019, which claims the benefit of U.S. Provisional Patent Application No. 62/673,693, filed May 18, 2018, the disclosure of each of which is incorporated by reference herein in its entirety.

I. FIELD

Provided herein are methods for preparing a desired enantiomer of 6-[amino(4-chlorophenyl)(1-methyl-1H-imidazol-5-yl)methyl]-4-(3-chlorophenyl)-1-methyl-2(1H)-quinolinone, otherwise known as tipifarnib.

II. BACKGROUND

Farnesyltransferase inhibitors block the main post-translational modification of the Ras protein, thus interfering with its localization to the inner surface of the plasma membrane and subsequent activation of the downstream effectors. Although initially developed as a strategy to target Ras in cancer, farnesyltransferase inhibitors have subsequently been acknowledged as acting by additional and more complex mechanisms that may extend beyond Ras involving GTP-binding proteins, kinases, centromere-binding proteins and probably other farnesylated proteins.

A particular farnesyltransferase inhibitor that has been described is (R)-(+)-6-[amino(4-chlorophenyl)(1-methyl-1H-imidazol-5-yl)methyl]-4-(3-chlorophenyl)-1-methyl-2(1H)-quinolinone, otherwise known as R115777 or (R)-(+)-tipifarnib. See WO 97/21701, the disclosure of which is incorporated herein by reference in its entirety. (R)-(+)-Tipifarnib is a potent, selective and orally bioavailable inhibitor of farnesyl transferase. It is one of the most advanced of the farnesyl transferase inhibitors currently reported to be in clinical development, being one of the agents that have progressed to phase III studies.

(R)-(+)-Tipifarnib has been found to have very potent activity against neoplastic diseases. Antineoplastic activity in solid tumors, as well as in hematological malignancies, have been observed.

The synthesis of (R)-(+)-tipifarnib as originally described in WO 97/21701, is presented in Scheme 1.

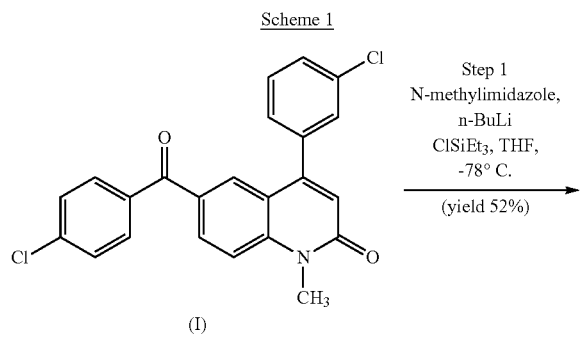

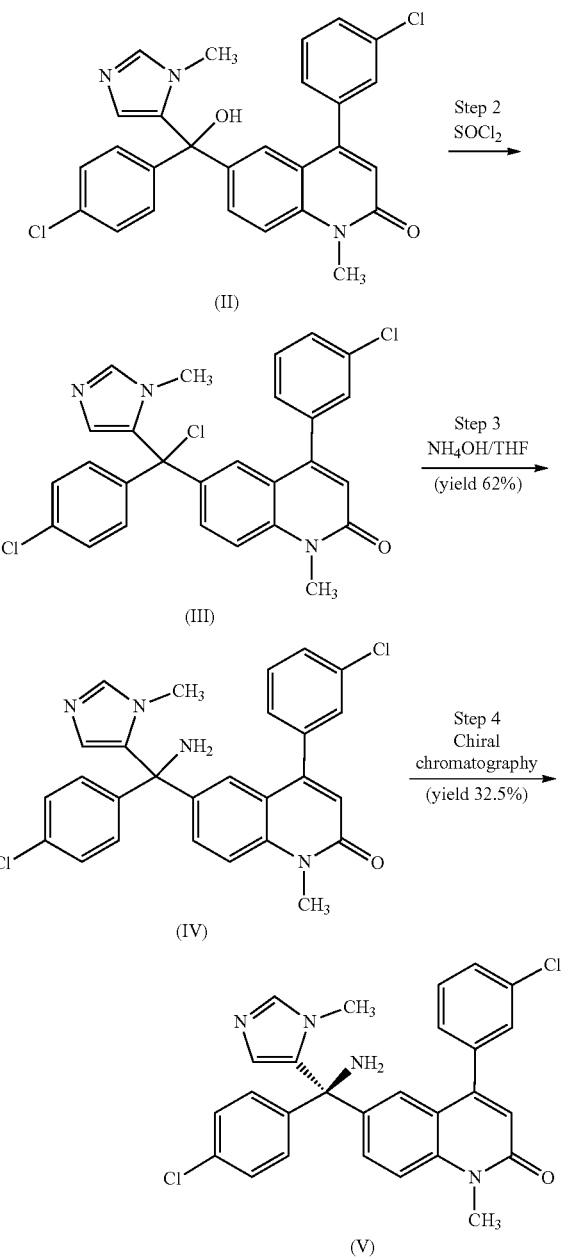

In this synthesis, tipifarnib is initially synthesized as a racemate (Step 3). Then, the enantiomers are separated to give the (R)-(+)-tipifarnib, although in only 32.5% yield.

The approach described above highlights a characteristic shortcoming of methods based on resolution of a racemate. Namely, the undesired (S)-(−)-enantiomer is discarded, resulting in low yield and added manufacturing costs. Thus, there is a need for improved methods of synthesizing (R)-(+)-tipifarnib.

III. SUMMARY

Provided herein are methods for preparing a desired enantiomer of 6-[amino(4-chlorophenyl)(1-methyl-1H-imidazol-5-yl)methyl]-4-(3-chlorophenyl)-1-methyl-2(1H)- quinolinone, otherwise known as tipifarnib. One embodiment comprises synthesizing racemic tipifarnib, crystallizing the desired enantiomer from the racemate, separating crystals of the desired enantiomer from a mother liquor, and racemizing and recycling of the undesired enantiomer in the mother liquor.

One embodiment is summarized and represented by Scheme 2, which is a synthetic scheme for the preparation of (R)-(+)-tipifarnib utilizing a racemic synthesis of tipifarnib, crystallization to resolve a racemic mixture of tipifarnib, and racemization and recycling of the mother liquor back into an intermediate stage in the racemic synthesis.

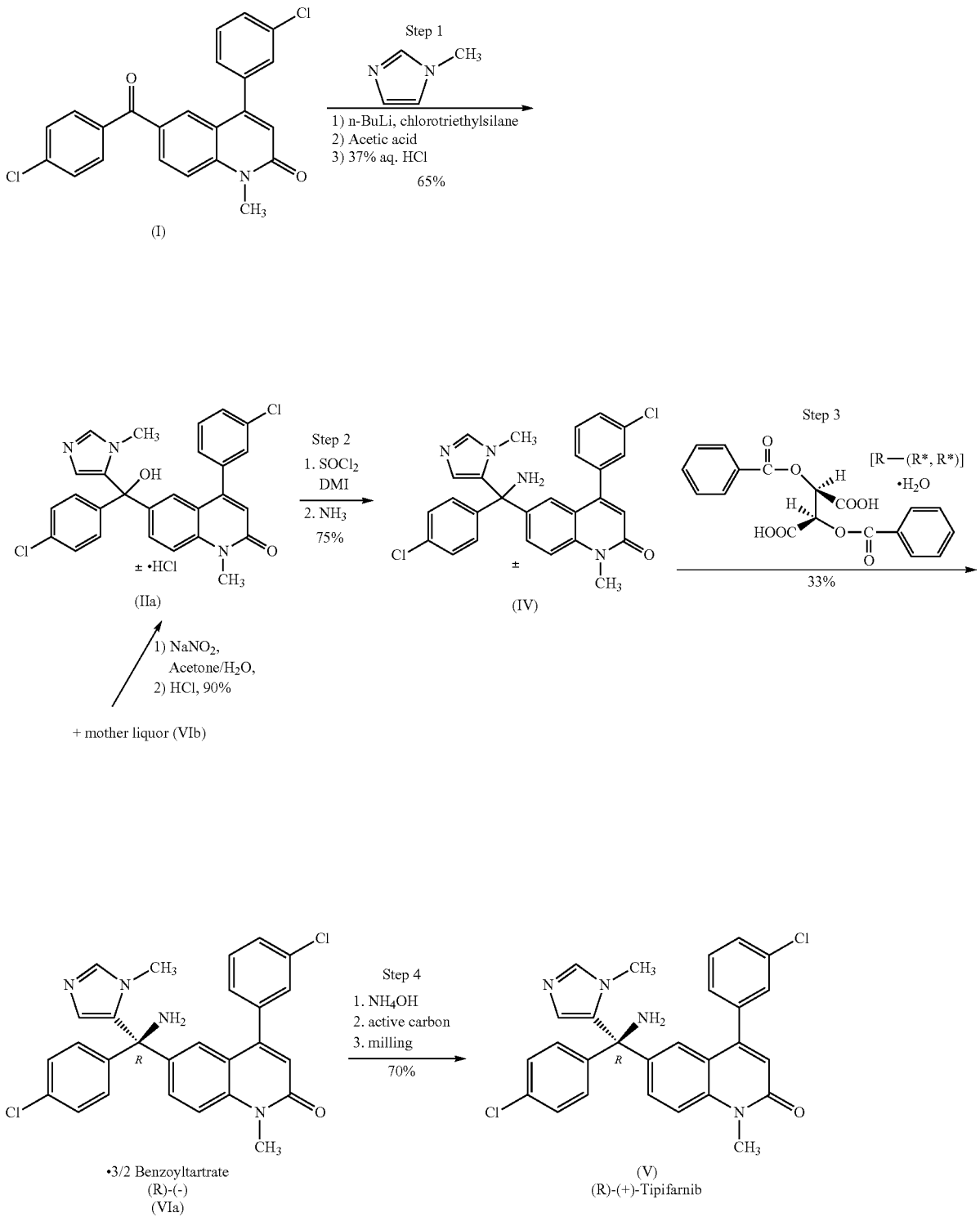

In another embodiment, summarized in Scheme 3, an alternative synthetic procedure is utilized to recycle the mother liquor (VIb) back into an intermediate stage in the racemic synthesis.

The term "enantiomer" refers to one of a pair of molecular entities which are mirror images of each other and non-superimposable.

Scheme 3

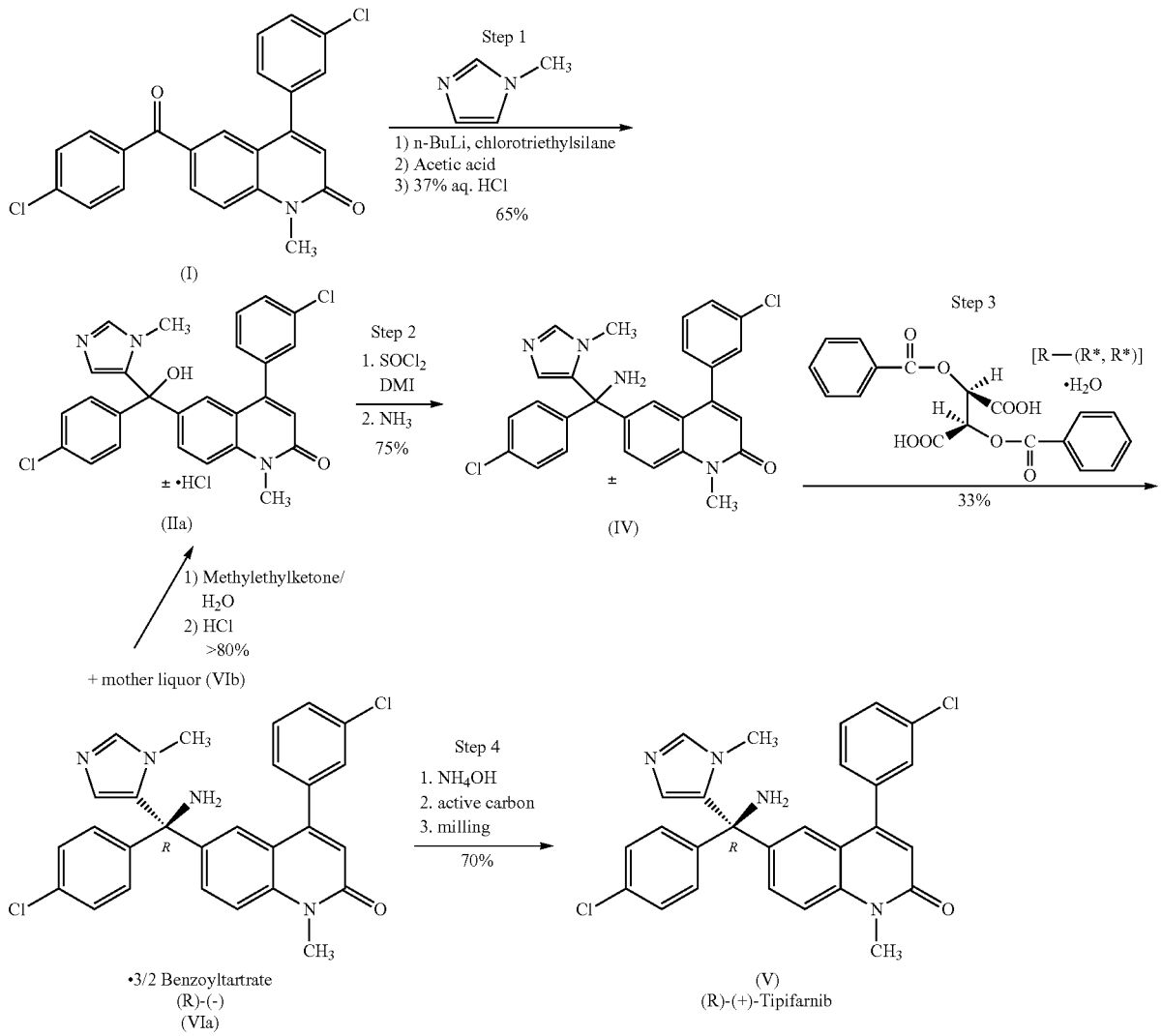

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

The descriptions of the terminology provided below apply to the terms as used herein and unless otherwise specified.

The term "stereochemical formula" refers to a three-dimensional view of a molecule either as such or in a projection. A pair of stereochemical formulae are "superimposable" when they can be brought into coincidence by no more than translation and rigid rotation.

The term "chirality" refers to the geometric property of a rigid object, such as spatial arrangement of atoms, of being non-superimposable on its mirror image. If the object is superimposable on its mirror image the object is described as being achiral.

The term "optical activity" refers to the ability of a sample of material to rotate the plane of polarization of a beam of transmitted plane-polarized light. This optical rotation is a sufficient but not necessary distinguishing characteristic of systems containing unequal amounts of corresponding enantiomers. An enantiomer causing rotation in a clockwise direction when viewed in the direction facing the oncoming light beam under specified conditions is called dextrorotatory and its chemical name or formula is designated by the prefix (+); one causing rotation in the opposite sense is levorotatory and designated by the prefix (−).

An enantiomer may also be designated by the prefix of either (R) or (S), which is deduced by application of the Cahn-Ingold-Prelog priority rules, the authoritative statement of which appears in R. S. Cahn, C. K. Ingold and V. Prelog, Angew. Chem. 78, 413-447 (1966), Angew. Chem. Internat. Ed. Eng. 5, 385-415, 511 (1966); and V. Prelog and G. Helmchen, Angew. Chem. 94, 614-631 (1982), Angew. Chem. Internat. Ed. Eng. 21, 567-583 (1982).

The term "enantiopure" or "enantiomerically pure" refers to a sample all of whose molecules have the same chirality sense within limits of detection.

The term "racemic mixture" or "racemate" refers to an equimolar mixture of a pair of enantiomers. A racemic mixture does not exhibit optical activity.

The term "enantiomeric excess" refers to the difference in mole factions of two opposite enantiomers in a composition. Enantiomeric excess is frequently expressed as a percentage.

The term "acid" refers to both Brønsted acid and Lewis acid. A Brønsted acid is a molecular entity capable of donating a hydron to a Brønsted base. A Lewis acid is a molecular entity that is an electron-pair acceptor and therefore able to react with a Lewis base to form a Lewis adduct, by sharing the electron pair furnished by the Lewis base.

The term "base" refers to both Brønsted base and Lewis base. A Brønsted base is a molecular entity capable of accepting a hydron from a Brønsted acid. A Lewis base is a molecular entity able to provide a pair of electrons and thus capable of coordination to a Lewis acid, thereby producing a Lewis adduct.

The term "hydron" is the general name for the cation $H^+$ used without regard to the nuclear mass of the hydrogen entity.

The term "salt" refers to a chemical compound consisting of an assembly of cations and anions.

The term "chiral resolving agent" refers to a reagent used to convert a mixture of enantiomers into diastereomers, usually by formation of a well-crystallizing diastereomeric salt.

The term "solvent" refers to a liquid in which a solute dissolves to form a solution.

The term "miscibility" refers to the ability of a mixture to form a single phase. Miscibility may be limited to certain ranges of temperature, pressure, and composition.

The terms "process" and "method" are used interchangeably to refer to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "resolution," "optical resolution," or "chiral resolution" are used interchangeably to refer to any process by which a racemic mixture is separated into its two constituent enantiomers.

The term "crystallization" refers to the formation of a crystalline solid from a solution, melt, vapor or a different solid phase, generally by the lowering of the temperature or by evaporation of a solvent.

The term "mother liquor" refers to the part of a solution that is left over after crystallizing from a solution. It is the liquid obtained by filtering away the crystals formed.

The term "extraction" refers to the process of transferring a substance from any matrix to an appropriate liquid phase. More specifically, it refers to liquid-liquid extraction, which is the process of transferring a solute from a liquid phase to another immiscible or partially miscible liquid phase in contact with it.

The terms "reacting" is used to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere (e.g., $N_2$ or Ar). In certain embodiments, the term "reacting" can also refer to in situ formation or intra-molecular reaction where the reactive groups are in the same molecule.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "compound" includes salt, solvates (e.g. hydrates), co-crystals, and polymorphs thereof.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a non-crystalline form. Where the solvent is water, the solvate is a hydrate. Examples of hydrates include, but are not limited to, a hemihydrate, monohydrate, dihydrate, trihydrate, tetrahydrate, and pentahydrate.

The term "polymorph" refers to solid crystalline forms of a compound or complex thereof. Different polymorphs of the same compound can exhibit different physical, chemical and spectroscopic properties.

If the stereochemistry of a structure or a portion thereof is not indicated, e.g., with bold or dashed lines, the structure or portion thereof is to be interpreted as encompassing all stereoisomers of the structure.

B. Methods of Preparation

In certain embodiments, provided herein is a method for preparing a desired enantiomer of tipifarnib comprising the steps of: (i) obtaining a starting material comprising tipifarnib that is not enantiopure in the desired enantiomer; (ii) transforming the starting material from step (i) to a racemic mixture of tipifarnib; and (iiii) recovering the desired enantiomer of tipifarnib from the racemic mixture of tipifarnib of step (ii). In one embodiment, the method is shown in Scheme 2. In one embodiment, the method is shown in Scheme 3.

In one embodiment, the desired enantiomer of tipifarnib is (R)-(+)-tipifarnib. In another embodiment as shown in Scheme 2, the desired enantiomer of tipifarnib is (R)-(+)-tipifarnib. In another embodiment as shown in Scheme 3, the desired enantiomer of tipifarnib is (R)-(+)-tipifarnib.

In certain embodiments, the starting material of step (i) comprises a mother liquor from a crystallization process. In certain embodiments, the starting material of step (i) comprises an enantiomeric excess of an undesired enantiomer of tipifarnib. In one embodiment, the undesired enantiomer of tipifarnib is (S)-(−)-tipifarnib. In another embodiment as shown in Scheme 2, the undesired enantiomer of tipifarnib is (S)-(−)-tipifarnib. In another embodiment as shown in Scheme 3, the undesired enantiomer of tipifarnib is (S)-(−)-tipifarnib.

In certain embodiments, the starting material of step (i) comprises a salt of tipifarnib formed with an acid. In certain embodiments, the acid is an enantiopure chiral organic acid. In certain embodiments, the acid is a chiral resolving agent. In one embodiment, the acid is (−)-dibenzoyl-L-tartaric acid. In another embodiment as shown in Scheme 2, the acid is (−)-dibenzoyl-L-tartaric acid. In another embodiment as shown in Scheme 3, the acid is (−)-dibenzoyl-L-tartaric acid.

In certain embodiments, step (ii) transforming the starting material to a racemic mixture of tipifarnib comprises the steps of: (ii)(a) reacting the starting material with sodium nitrite in a reaction solvent to give a product mixture; (ii)(b) recovering a racemic alcohol of Formula (II) from the product mixture of step (ii)(a); and (ii)(c) transforming the racemic alcohol of step (ii)(b) to the racemic mixture of tipifarnib. In one embodiment, the steps are shown in Scheme 2.

In certain embodiments, step (ii) transforming the starting material to a racemic mixture of tipifarnib comprises the steps of: (ii)(a) heating the starting material in an aqueous reaction solvent to give a product mixture; (ii)(b) recovering a racemic alcohol of Formula (II) or (IIa) from the product mixture of step (ii)(a); and (ii)(c) transforming the racemic alcohol of step (ii)(b) to the racemic mixture of tipifarnib of Formula (IV). In one embodiment, the steps are shown in Scheme 3.

In certain embodiments, the reaction solvent of step (ii)(a) is an organic solvent, water, or a mixture thereof. In one embodiment, the reaction solvent of step (ii)(a) is a mixture of an organic solvent and water. In certain embodiments, the mixture has a volume ratio of organic solvent to water in a range from 20:1 to 3.5:1. In another embodiment, the volume ratio of organic solvent to water is 4:1. In one embodiment as shown in Scheme 2, the volume ratio of organic solvent to water is 4:1. In certain embodiments, the mixture has a volume ratio of organic solvent to water in a range from 6:1 to 2:1. In one embodiment, the volume ratio of organic solvent to water is 2:1. In another embodiment as shown in Scheme 3, the volume ratio of organic solvent to water is 2:1.

In certain embodiments, the organic solvent is miscible with water. In some embodiments, the organic solvent is acetone, acetonitrile, methanol, tert-amyl alcohol, or a mixture thereof. In one embodiment, the organic solvent is acetone. In another embodiment, the organic solvent is acetonitrile. In another embodiment as shown in Scheme 2, the organic solvent is acetone. In some embodiments, the organic solvent is acetonitrile, methylethylketone, acetone, DMF, or a mixture thereof. In one embodiment, the organic solvent is methylethylketone. In one embodiment as shown in Scheme 3, the organic solvent is methylethylketone.

In certain embodiments, the reaction of step (ii)(a) takes place at a temperature ranging from about 20° C. to about 75° C. In one embodiment, the reaction of step (ii)(a) takes place at a temperature of about 20° C. In another embodiment, the reaction of step (ii)(a) takes place at a temperature of 20° C. In another embodiment as shown in Scheme 2, the reaction takes place at a temperature of 20° C. In certain embodiments, the reaction of step (ii)(a) takes place at a temperature ranging from about 60° C. to about 80° C. In one embodiment, the reaction of step (ii)(a) takes place at a temperature of about 80° C. In another embodiment, the reaction of step (ii)(a) takes place at a temperature of about 76° C. In another embodiment as shown in Scheme 3, the reaction takes place at a temperature of about 76° C.

In certain embodiments, the reaction of step (ii)(a) takes place in the presence of an additive. In certain embodiments, the additive is an acid. In one embodiment, the acid is sulfuric acid. In another embodiment, the acid is hydrochloric acid. In another embodiment, the acid is 50% sulfuric acid. In another embodiment, the acid is 37% hydrochloric acid.

In certain embodiments, step (ii)(b) recovers the racemic alcohol of Formula (II) in the form of a salt. In one embodiment, step (ii)(b) recovers the racemic alcohol of Formula (II) in the form of a hydrochloride salt. In another embodiment, step (ii)(b) recovers a salt of Formula (IIa). In another embodiment as shown in Scheme 2, a salt of Formula (IIa) is recovered. In another embodiment as shown in Scheme 3, a salt of Formula (IIa) is recovered.

In certain embodiments, step (ii)(b) recovering a racemic alcohol of Formula (II) from the product mixture of step (ii)(a) comprises the steps of: adjusting the product mixture's pH with a base; extracting the product mixture with an extraction solvent; and crystallizing the racemic alcohol of Formula (II).

In certain embodiments, the product mixture's pH is adjusted to a range from about 5 to about 10. In one embodiment, the product mixture's pH is adjusted to about 10. In one embodiment, the product mixture's pH is adjusted to about 8. In another embodiment, the product mixture's pH is adjusted to 10.

In certain embodiments, the base is sodium hydroxide or ammonium hydroxide. In one embodiment, the base is sodium hydroxide. In another embodiment, the base is 10% aqueous sodium hydroxide.

In certain embodiments, the extraction solvent is isopropyl acetate or 2-methyltetrahydrofuran. In one embodiment, the extraction solvent is isopropyl acetate.

In certain embodiments, the racemic alcohol is crystallized as a hydrochloride salt. In one embodiment as shown in Scheme 2, the racemic alcohol is crystallized as a hydrochloride salt of Formula (IIa). In another embodiment as shown in Scheme 3, the racemic alcohol is crystallized as a hydrochloride salt of Formula (IIa).

In certain embodiments, step (ii) transforming the starting material to a racemic mixture of tipifarnib comprises the steps of: (ii)(a) reacting the starting material with sodium nitrite in a reaction solvent to give a product mixture; (ii)(b) recovering a racemic alcohol of Formula (II) from the product mixture of step (ii)(a); and (ii)(c) transforming the racemic alcohol of step (ii)(b) to the racemic mixture of tipifarnib. In one embodiment, the steps are shown in Scheme 2.

In certain embodiments, the reaction solvent of step (ii)(a) is an organic solvent, water, or a mixture thereof. In one embodiment, the reaction solvent of step (ii)(a) is a mixture of an organic solvent and water. In certain embodiments, the mixture has a volume ratio of organic solvent to water in a range from 20:1 to 3.5:1. In another embodiment, the volume ratio of organic solvent to water is 4:1. In another embodiment as shown in Scheme 2, the volume ratio of organic solvent to water is 4:1.

In certain embodiments, the organic solvent is miscible with water. In some embodiments, the organic solvent is acetone, acetonitrile, methanol, tert-amyl alcohol, or a mixture thereof. In one embodiment, the organic solvent is acetone. In another embodiment, the organic solvent is acetonitrile. In another embodiment as shown in Scheme 2, the organic solvent is acetone.

In certain embodiments, the reaction of step (ii)(a) takes place at a temperature ranging from about 20° C. to about 75° C. In one embodiment, the reaction of step (ii)(a) takes place at a temperature of about 20° C. In another embodiment, the reaction of step (ii)(a) takes place at a temperature of 20° C. In another embodiment as shown in Scheme 2, the reaction takes place at a temperature of 20° C.

In certain embodiments, the reaction of step (ii)(a) takes place in the presence of an additive. In certain embodiments, the additive is an acid. In one embodiment, the acid is sulfuric acid. In another embodiment, the acid is hydrochloric acid. In another embodiment, the acid is 50% sulfuric acid. In another embodiment, the acid is 37% hydrochloric acid.

In certain embodiments, step (ii)(b) recovers the racemic alcohol of Formula (II) in the form of a salt. In one embodiment, step (ii)(b) recovers the racemic alcohol of Formula (II) in the form of a hydrochloride salt. In another embodiment, step (ii)(b) recovers a salt of Formula (IIa). In another embodiment as shown in Scheme 2, a salt of Formula (IIa) is recovered.

In certain embodiments, step (ii)(b) recovering a racemic alcohol of Formula (II) from the product mixture of step (ii)(a) comprises the steps of: adjusting the product mixture's pH with a base; extracting the product mixture with an extraction solvent; and crystallizing the racemic alcohol of Formula (II)

In certain embodiments, the product mixture's pH is adjusted to a range from about 5 to about 10. In one embodiment, the product mixture's pH is adjusted to about 10. In another embodiment, the product mixture's pH is adjusted to 10.

In certain embodiments, the base is sodium hydroxide or ammonium hydroxide. In one embodiment, the base is sodium hydroxide. In another embodiment, the base is 10% aqueous sodium hydroxide.

In certain embodiments, the extraction solvent is isopropyl acetate or 2-methyltetrahydrofuran. In one embodiment, the extraction solvent is isopropyl acetate.

In certain embodiments, the racemic alcohol is crystallized as a hydrochloride salt. In one embodiment as shown in Scheme 2, a hydrochloride salt (IIa) of the racemic alcohol is crystallized.

In certain embodiments, step (iii) recovering the desired enantiomer of tipifarnib from the racemic mixture comprises: (iii)(a) crystallizing the desired enantiomer of tipifarnib from the racemic mixture of tipifarnib in the presence of a chiral resolving agent; and (iii)(b) separating crystals of the desired enantiomer of tipifarnib from a mother liquor. In one embodiment, the steps are shown in Scheme 2. In another embodiment, the steps are shown in Scheme 3.

In certain embodiments, the chiral resolving agent of step (iii)(a) is an enantiopure chiral organic acid. In one embodiment, the chiral resolving agent of step (iii)(a) is (−)-dibenzoyl-L-tartaric acid. In another embodiment as shown in Scheme 2, the chiral resolving agent of step (iii)(a) is (−)-dibenzoyl-L-tartaric acid. In another embodiment as shown in Scheme 3, the chiral resolving agent of step (iii)(a) is (−)-dibenzoyl-L-tartaric acid.

In certain embodiments, the mother liquor of step (iii)(a) comprises an enantiomeric excess of an undesired enantiomer of tipifarnib. In one embodiment, the undesired enantiomer of tipifarnib is (S)-(−)-tipifarnib. In another embodiment as shown in Scheme 2, the undesired enantiomer of tipifarnib is (S)-(−)-tipifarnib. In another embodiment as shown in Scheme 3, the undesired enantiomer of tipifarnib is (S)-(−)-tipifarnib.

In certain embodiments, the method further comprises: (iv) recycling the mother liquor of step (iii)(b) to be used as the starting material in step (i). In certain embodiments, the steps (i) to (iv) may be run in multiple cycles. In one embodiment, the method is shown in Scheme 2. The another embodiment, the method is shown in Scheme 3.

In certain embodiments, provided herein is a method for preparing a desired enantiomer of tipifarnib comprising the steps of: (i) obtaining a starting material comprising tipifarnib that is not enantiopure in the desired enantiomer; (ii)(a) reacting the starting material with sodium nitrite to give a product mixture; (ii)(b) recovering a racemic alcohol of Formula (II) from the product mixture of step (ii)(a); (ii)(c) transforming the racemic alcohol of step (ii)(b) to a racemic mixture of tipifarnib; (iii)(a) crystallizing the desired enantiomer of tipifarnib from the racemic mixture of tipifarnib of step (ii)(c) in the presence of a chiral resolving agent; (iii)(b) separating crystals of the desired enantiomer of tipifarnib from the mother liquor of step (iii)(a); and (iv) recycling the mother liquor of step (iii)(b) to be used as the starting material in step (i). In one embodiment, the method is shown in Scheme 2.

In certain embodiments, provided herein is a method for preparing a desired enantiomer of tipifarnib comprising the steps of: (i) preparing a racemic mixture of tipifarnib; (ii) crystallizing the desired enantiomer of tipifarnib from the racemic mixture of tipifarnib of step (i) in the presence of a chiral resolving agent; (iii) separating crystals of the desired enantiomer of tipifarnib from a mother liquor; (iv) transforming any remaining tipifarnib in the mother liquor from step (iii) to a racemic alcohol of Formula (II); (v) transforming the racemic alcohol of step (iv) to a racemic mixture of tipifarnib; and (vi) recycling the racemic mixture of tipifarnib of step (v) back to step (i). In one embodiment, the method is shown in Scheme 2. In another embodiment, the method is shown in Scheme 3.

In certain embodiments, provided herein is a method for transforming an enantiomerically enriched amine of Formula (IV) comprising: (i) reacting the enantiomerically enriched amine of Formula (IV) or its salt with sodium nitrite in a 4:1 mixture of acetone and water at 20° C. to afford a product mixture; (ii) adjusting the product mixture's pH to about 10 with sodium hydroxide; (iii) extracting the product mixture with isopropyl acetate; (iv) adding 1.5 equivalents of concentrated hydrochloric acid; and (v) recovering a racemic alcohol of Formula (IIa) by crystallization. In one embodiment, the method provided herein suppresses the formation of the major impurity of Formula (VII). In another embodiment, the method is shown in Scheme 2.

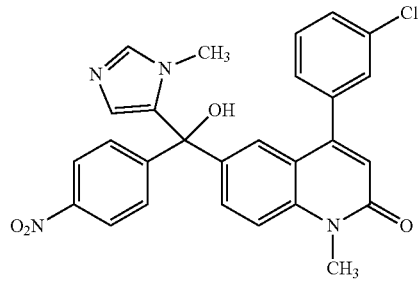

Formula (VII)

In certain embodiments, provided herein is a method for transforming an enantiomerically enriched amine of Formula (IV) comprising: (i) heating the enantiomerically enriched amine of Formula (IV) or its salt in a 2:1 mixture of methylethylketone and water at 76° C. to afford a product mixture; (ii) adjusting the product mixture's pH to about 8 with sodium hydroxide; (iii) extracting the product mixture with isopropyl acetate; (iv) adding concentrated hydrochloric acid; and (v) recovering a racemic alcohol of Formula (IIa) by crystallization. In one embodiment, the method is shown in Scheme 3.

V. EXAMPLES

Certain embodiments are illustrated by the following non-limiting examples. The discussion below is offered to illustrate certain aspects of the present invention and is not intended to limit the scope of the present invention. Changes can be made to the embodiments in light of the detailed description below. Although specific embodiments have been described herein for purposes of illustration, various modifications of the modes described herein for carrying out the disclosure that are obvious to persons of skill in the art are intended to be within the scope of the claims. All publications, patents, and patent applications cited in this specification are incorporated herein by reference as if each such publication, patent, or patent application were specifically and individually indicated to be incorporated herein by reference.

Hereinafter "eq." or "X" means equivalent or equivalents; "h" means hour or hours; "IPC" means in process control; "N.D." means not detected; "RT" means retention time; "temp." means temperature, and "V" means volume or volumes.

Example A1

Synthesis of (±)-4-(3-chlorophenyl)-6-[(4-chlorophenyl)hydroxy(1-methyl-1H-imidazol-5-yl)methyl]-1-methyl-2(1H)-quinolinone monohydrochloride (IIa)

As illustrated in Scheme 2, the transformation from 6-(4-chlorobenzoyl)-4-(3-chlorophenyl)-1-methyl-2(1H)-quinolinone (I) to (±)-4-(3-chlorophenyl)-6-[(4-chlorophenyl)hydroxy(1-methyl-1H-imidazol-5-yl)methyl]-1-methyl-2(1H)-quinolinone monohydrochloride (IIa) consists of two consecutive steps:

The first step was the condensation of 6-(4-chlorobenzoyl)-4-(3-chlorophenyl)-1-methyl-2(1H)-quinolinone (I) with 1-methyl-imidazole in the presence of n-butyllithium in hexane 23% and chlorotriethylsilane using tetrahydrofuran as solvent. After completion of the reaction, the reaction mixture was diluted with water and neutralized with acetic acid. After separation of the layers, water was added to the organic layer and it was neutralized with sodium hydroxide. The layers were separated and the organic layer was evaporated.

In the second step, the residue was diluted with 2-propanone. Formation of the hydrochloric acid salt (IIa) was performed by addition of hydrochloric acid. The product was crystallized. The precipitate was isolated, washed with 2-propanone and dried.

Specifically, hydrochloride (IIa) was prepared as follows:
1. Charge a reactor with minimum 1.7 L tetrahydrofuran and 1.75 moles 1-methylimidazole, stir and cool.
2. Add 0.11 kg n-butyllithium in hexane 23% (1.75 moles) and stir.
3. Add 0.27 kg chlorotriethylsilane (1.8 moles) and stir.
4. Add 0.10 kg n-butyllithium in hexane 23% (1.55 moles) at −75° C. to −68° C. and stir.
5. Charge another reactor with 1 mole ketone (I) and minimum 2 L tetrahydrofuran.
6. Stir and heat until ketone (I) is completely dissolved.
7. Cool and add the solution to the reaction mixture of step 4 while keeping the temperature at −75° C. to −68° C. and stir.
8. Add water and stir.
9. Add glacial acetic acid and stir.
10. Allow the layers to settle. Separate the layers. Discard the aqueous layer.
11. Add water and sodium hydroxide 29% to the organic layer and stir.
12. Allow the layers to settle. Separate the layers. Discard the aqueous layer.
13. Evaporate the organic layer.
14. Add 2-propanone and evaporate.
15. Repeat step 14 twice.
16. Add minimum 4 L 2-propanone to the evaporated residue, stir and cool.
17. Add hydrochloric acid and stir.
18. Centrifuge the precipitate and wash the product with 2-propanone.
19. Dry the product in a suitable drying unit.

The above described process was scaled to accommodate 549 to 822 moles of ketone (I). The process yielded 45-69% of alcohol (IIa).

Example A2

Synthesis of (±)-6-[amino(4-chlorophenyl)(1-methyl-1H-imidazol-5-yl)methyl]-4-(3-chlorophenyl)-1-methyl-2(1H)-quinolinone (IV)

As illustrated in Scheme 2, the transformation from (±)-4-(3-chlorophenyl)-6-[(4-chlorophenyl)hydroxy(1-methyl-1H-imidazol-5-yl)methyl]-1-methyl-2(1H)-quinolinone monohydrochloride (IIa) to (±)-6-[amino(4-chlorophenyl)(1-methyl-1H-imidazol-5-yl)methyl]-4-(3-chlorophenyl)-1-methyl-2(1H)-quinolinone (IV) consists of two consecutive steps:

The first step was the chlorination of alcohol (IIa) with thionylchloride in 1,3-dimethyl-2-imidazolidinone as solvent.

The second step was the amination of the in-situ intermediate chloride (III) (not shown in Scheme 2) to amine (IV) using a solution of ammonia in methanol. The product was crystallized by addition of water. The precipitate was isolated, washed with water and dried.

Specifically, amine (IV) was prepared as follows:
1. Charge a reactor with 2 L 1,3-dimethyl-2-imidazolidinone and 1 mole hydrochloride (IIa) and stir.
2. Add minimum 0.26 kg thionylchloride (2.2 moles) while keeping the temperature below 45° C.
3. Stir at 20-45° C. for at least 3 hours.
4. Charge another reactor with minimum 1.71 L ammonia in methanol (12 moles), stir and cool.
5. Add the reaction mixture from step 3 while keeping the temperature below 45° C.
6. Stir at 12-45° C. for at least 15 hours.
7. Add maximum 5 L water and stir.
8. Centrifuge the product and wash each centrifuge load with water.
9. Dry the product in a suitable drying unit.

The above described process was scaled to accommodate 480 to 720 moles of alcohol (IIa). The process yielded 65-85% of amine (IV).

Example A3

Synthesis of (R)-6-[amino(4-chlorophenyl)(1-methyl-1H-imidazol-5-yl)methyl]-4-(3-chlorophenyl)-1-methyl-2(1H)-quinolinone [R-(R*,R*)]-2,3-bis(benzoyloxy)butanedioate (2:3) (VIa)

As illustrated in Scheme 2, the transformation from (±)-6-[amino(4-chlorophenyl)(1-methyl-1H-imidazol-5-yl)

methyl]-4-(3-chlorophenyl)-1-methyl-2(1H)-quinolinone (IV) to (R)-6-[amino(4-chlorophenyl)(1-methyl-1H-imidazol-5-yl)methyl]-4-(3-chlorophenyl)-1-methyl-2(1H)-quinolinone [R-(R*,R*)]-2,3-bis(benzoyloxy)butanedioate (2:3) (VIa) consisted of the formation of the [R-(R*,R*)]-2,3-bis(benzoyloxy)-butanedioic acid salt of amine (IV) with [R-(R*,R*)]-2,3-bis(benzoyloxy)-butanedioic acid monohydrate using 2-propanone as solvent. The product was isolated, washed with 2-propanone and dried.

Specifically, salt (VIa) was prepared as follows:

1. Charge a reactor with minimum 3.6 L 2-propanone, 1 mole amine (IV) and minimum 2.8 moles [R-(R*,R*)]-2,3-bis(benzoyloxy)butanedioic acid monohydrate and stir at a maximum temperature of 25° C.
2. Centrifuge the product and wash each centrifuge load with 2-propanone.
3. Collected the filtrate as mother liquor (VIb).
4. Dry the product in a suitable drying unit.

The above described process was scaled to accommodate 460 to 1255 moles of amine (IV). The process yielded 27-37% of salt (VIa).

Example A4

Synthesis of "crude" (R)-6-[amino(4-chlorophenyl)(1-methyl-1H-imidazol-5-yl)methyl]-4-(3-chlorophenyl)-1-methyl-2(1H)-quinolinone (V)

As illustrated in Scheme 2, the transformation from (R)-6-[amino(4-chlorophenyl)(1-methyl-1H-imidazol-5-yl)methyl]-4-(3-chlorophenyl)-1-methyl-2(1H)-quinolinone [R-(R*,R*)]-2,3-bis(benzoyloxy)butanedioate (2:3) (VIa) to "crude" (R)-6-[amino(4-chlorophenyl)(1-methyl-1H-imidazol-5-yl)methyl]-4-(3-chlorophenyl)-1-methyl-2(1H)-quinolinone (V) consisted of the liberation of the base of salt (VIa) with ammonium hydroxide using a mixture of water and ethanol as solvent. The product was crystallized by cooling. The precipitate was isolated, washed with water and dried.

Specifically, "crude" (R)-(+)-tipifarnib (V) was prepared as follows:

1. Charge a reactor with ethanol anhydrous denatured and 1 mole salt (VIa) and stir.
2. Add ammonium hydroxide.
3. Add water, heat to reflux and reflux for maximum 150 minutes.
4. Cool and stir.
5. Centrifuge the product and wash each centrifuge load with water.
6. Dry the product in a suitable drying unit.

The above described process was scaled to accommodate 147 to 706 moles of salt (VIa). The process yielded 70-95% of "crude" (V).

Example A5

Synthesis of "not milled" (R)-6-[amino(4-chlorophenyl)(1-methyl-1H-imidazol-5-yl)methyl]-4-(3-chlorophenyl)-1-methyl-2(1H)-quinolinone (V)

As illustrated in Scheme 2, "crude" (R)-6-[amino(4-chlorophenyl)(1-methyl-1H-imidazol-5-yl)methyl]-4-(3-chlorophenyl)-1-methyl-2(1H)-quinolinone (V) was dissolved in ethanol and treated with activated carbon. After filtration over infusorial earth, the reaction mixture was partly evaporated. The product was crystallized by cooling. The precipitate was isolated and washed with ethanol. The wet product was again dissolved in ethanol and treated with activated carbon. After filtration over infusorial earth, the reaction mixture was partly evaporated. The product was crystallized by cooling. The precipitate was isolated, washed with ethanol and dried.

Specifically, "not milled" (R)-(+)-tipifarnib (V) was prepared as follows:

1. Charge a reactor with ethanol anhydrous denatured, 1 mole crude (V), minimum 12.5 g activated carbon type norit A supra, infusorial earth and stir.
2. Heat to reflux and reflux while stirring.
3. Filter the reaction mixture to another reactor, wash the filter with ethanol anhydrous denatured, stir and evaporate maximum 5.72 L solvent over a period of maximum 24 hours.
4. Cool and stir.
5. Centrifuge the product and wash each centrifuge load with ethanol anhydrous denatured.
6. Charge a reactor with ethanol anhydrous denatured, the wet product from step 5, minimum 12.5 g activated carbon type norit A supra, infusorial earth and stir.
7. Heat to reflux and reflux while stirring.
8. Filter the reaction mixture to another reactor, wash the filter with ethanol anhydrous denatured, stir and evaporate maximum 5.43 L solvent over a period of maximum 24 hours.
9. Repeat steps 4 and 5.
10. Dry the product in a suitable drying unit until the loss on drying ≤0.20% w/w.

The above described process was scaled to accommodate 392 to 588 moles of "crude" (V). The process yielded of 69-84% of "not milled" (V).

Example A6

Synthesis of (R)-(+)-tipifarnib (V)

As illustrated in Scheme 2, "not milled" (R)-6-[amino(4-chlorophenyl)(1-methyl-1H-imidazol-5-yl)methyl]-4-(3-chlorophenyl)-1-methyl-2(1H)-quinolinone (V) was milled, and optionally sieved and homogenized.

As milling is a semi-continuous flow-through process, there was not a typical batch size. The process yielded 90% or higher of (V).

Example B1

Feasibility Study on Recovery of Mother Liquor

In order to recover the undesired enantiomer in the form of a dibenzoyltartrate salt (VIb) in the mother liquor and realize the transformation from salt (VIb) of the undesired enantiomer to alcohol (IIa) (see Scheme 2), several experiments were conducted to study the feasibility of the proposed recovery and transformation process. The details of the experiments are summarized in Tables 1, 2 and 3. The experiments were first conducted using salt (VIa) of the desired enantiomer.

TABLE 1

Racemization of VIa without NaNO$_2$

| Batch No. | Materials | | | | IPC (IV/II) %* | |
|---|---|---|---|---|---|---|
| | VIa | H$_2$O | MeOH | Acid | 19 h at 40° C. | 4 h at 75° C. |
| T1-1 | 1.5 g 1.0 X Solid | 4.5 mL 3 V | 15 mL 10 V | | 64.22/18.43 | 3.24/50.55 |
| | VIa | H$_2$O | acetone | Acid | 2 h at 50° C. | 18 h at 50° C. | 24 h at 50° C. |
| T1-2 | 1.0 g 1.0 X Solid | 20 mL 20 V | | | 96.32/2.99 | 86.15/13.01 | 71.66/27.07 |
| T1-3 | | 20 mL 20 V | | 0.1 mL 37% HCl | 97.57/1.96 | 86.39/12.81 | 69.28/29.53 |
| T1-4 | | 1 mL 1 V | 20 mL 20 V | | 90.55/5.62 | 68.51/19.64 | 44.28/36.51 |

*Determined by peak area integration of HPLC graph.

In Experiment T1-1, 10 volumes of methanol and 3 volumes of water were used as the solvent, and the reaction was conducted at 40° C. and 75° C. In Experiment T1-2, 20 volumes of water was used as the solvent. In Experiment T1-3, 0.1 mL of concentrated hydrochloric acid was used as an additive. In Experiment T1-4, 1 volume of water and 20 volumes of acetone were used as the solvent. The last three experiments T1-2/3/4 were conducted at 50° C.

The data from Experiment T1-1 indicate that conversion from salt (VIa) to alcohol (II) is feasible. Furthermore, analysis of alcohol (II) with chiral chromatography demonstrates complete racemization of the chiral center. However, the reaction conditions lead to the formation of significant amounts of impurities.

The data from Experiments T1-2/3/4 indicate that racemization without sodium nitrite has a low conversion rate even with the help of acid at 50° C. For example in Experiment T1-3, only about 30% of alcohol (II) was observed after stirring at 50° C. for 24 hours.

Further experiments employed sodium nitrite as an oxidant in an attempt to improve the reaction conversion and purity profile. Details of the experiments are summarized in Table 2.

Five experiments were conducted using salt (VIa), and 1.5 equivalents of sodium nitrite were used as a reaction reagent. In Experiment T2-2, 20 volumes of tert-amyl alcohol and 1 volume of water were used as the solvent. In Experiment T2-3, 20 volumes of acetone and 1 volume of water were used as the solvent. In Experiment T2-4, 20 volumes of acetonitrile and 1 volume of water were used as the solvent. In Experiment T2-5, 20 volumes of acetonitrile and 1 volume of water were used as the solvent, and 2.0 equivalents of sulfuric acid were used as an additional additive. Experiments T2-2/3/4/5 were conducted at 20° C.

As the data in Table 2 reveal, sodium nitrite can convert the desired enantiomer salt (VIa) to alcohol (II) at a mild temperature of 20° C. In particular, almost all the starting material in Experiment T2-5 was converted to alcohol (II) after stirring at 20° C. for 2 hours. Furthermore, analysis of alcohol (II) with chiral chromatography demonstrates complete racemization of the chiral center.

Further experiments employed the mother liquor containing salt (VIb) to investigate the recovery process directly. The details of these experiments are summarized in Table 3.

TABLE 2

Racemization of VIa with NaNO$_2$

| Batch No. | Materials | | | | IPC (IV/II) %* |
|---|---|---|---|---|---|
| | VIa | NaNO$_2$ | Solvent | Acid | 39 h at 20° C. |
| T2-1 | 1.5 g 1.0 X Solid | 0.3 g | 15 mL MeOH 4.5 mL H$_2$O | | 80.32/16.10 |
| | VIa | NaNO$_2$ | Solvent | Acid | 2 h at 20° C. | 18 h at 20° C. | 24 h at 20° C. |
| T2-2 | 1.0 g 1.0 X Solid | 0.1 g 1.5 eq. | 20 mL t-AmOH 1 mL H$_2$O | | 42.38/48.69 | 49.24/41.76 | 29.57/57.89 |
| T2-3 | | | 20 mL Acetone 1 mL H$_2$O | | 16.65/72.77 | 24.17/64.75 | 20.23/69.23 |
| T2-4 | | | 20 mL MeCN 1 mL H$_2$O | | 36.53/60.72 | 38.40/59.03 | 36.10/61.15 |
| T2-5 | | | 20 mL MeCN 1 mL H$_2$O | H$_2$SO$_4$ 2.0 eq. | 1.67/92.55 | 0.11/97.41 | |

*Determined by peak area integration of HPLC graph.

TABLE 3

Racemization of mother liquor with NaNO₂

| Batch No. | Materials | | | | IPC (IV/II) %* | | | |
|---|---|---|---|---|---|---|---|---|
| | | | | | Solution | | | |
| | VIb | NaNO₂ | 50% H₂SO₄ | Solvent | Initial purity | after solvent switch | 2 h at 20° C. | 18 h at 20° C. |
| T3-1 | 1.0 X Mother liquor | 0.16 g 1.5 eq. | | 20 mL Acetone 1 mL H₂O | 89.93/1.16 | | 15.60/74.10 | 0.54/87.86 |
| T3-2 | | | 2.0 eq. | 20 mL MeCN 1 mL H₂O | | 85.55/4.34 | 0.51/89.61 | 0.48/90.02 |

*Determined by peak area integration of HPLC graph.

In Experiment T3-1, 20 mL of acetone and 1 mL of water were used as the solvent. In Experiment T3-2, 20 mL of acetonitrile and 1 mL of water were used as the solvent, and 2.0 equivalents of sulfuric acid were used as an additive. Both of these experiments were conducted at 20° C.

As summarized in Table 3, almost all the starting material was converted to alcohol (II) after stirring at 20° C. for 18 h in both experiments. Chiral HPLC confirmed that the product alcohol (II) was racemic in both experiments. Using acetone or acetonitrile as the solvent gave similar in-process control results.

Example B2

Investigating the Process Parameters for Working Up the Racemization Reaction

In order to find a suitable method to work up the reaction, several experiments were conducted using the solution from T2-5. Details of these experiments are summarized in Table 4, wherein "DBTA" refers to dibenzoyltartaric acid.

TABLE 4

Process parameters for working up the racemization reaction

| Batch No. | Materials for work-up | | | | Purity (DBTA/II) %* | | |
|---|---|---|---|---|---|---|---|
| | | | | | Solution before work-up | Solution after work-up and phase separation | |
| | II | Solvent | base | pH | (including DBTA) | Organic layer | Aqueous layer |
| T4-1 | 1 mL | 2 mL iPrOAc | 10% | 5 | 35.20/63.22 | 16.70/79.60 | 85.24/13.92 |
| T4-2 | T2-5 | 1 mL H₂O | NaOH | 7 | | 0.31/95.48 | 89.70/7.63 |
| T4-3 | | | | 10 | | 0.14/95.66 | 80.92/15.89 |
| T4-4 | | | NH₃•H₂O | | | 0.15/95.57 | 90.59/8.02 |
| T4-5 | | 2 mL 2-MeTHF 1 mL H₂O | 10% NaOH | | | 3.77/93.23 | 89.05/3.23 |

*Determined by peak area integration of HPLC graph.

In Experiments T4-1/2/3, the reaction mixture was diluted with 2 volumes of isopropyl acetate and 1 volume of water, and then treated with 10% sodium hydroxide to adjust the mixture's pH value. In Experiment T4-4, the reaction mixture was diluted with 2 volumes of isopropyl acetate and 1 volume of water, and then treated with ammonium hydroxide to adjust the mixture's pH to about 10. In Experiment T4-5, the reaction mixture was diluted with 2 volumes of 2-methyltetrahydrofuran and 1 volume of water, and then treated with 10% sodium hydroxide to adjust the mixture's pH to about 10.

A few observations can be made from the experimental data in Table 4. First, pH 5 is not a suitable pH point for work-up since as much as 16.70% of DBTA remains in the organic layer. Good separation is obtained at pH values from about 7 to about 10, where the amount of residual DBTA in the organic layer is below 1% when isopropyl acetate is used. Second, any residual alcohol (II) in aqueous layer may be recovered by back extraction of the aqueous layer. Last, using 2-methyltetrahydrofuran resulted in 3.77% of residual DBTA in the organic layer.

It is determined from these experiments that isopropyl acetate and 10% sodium hydroxide are the optimal materials for the work-up procedure, and pH adjustment to about 10 can ensure effective removal of DBTA.

Example B3

Optimization of the Recovery Process

Six experiments were conducted at different temperatures and with different solvents in order to further optimize the reaction conditions. The details of these experiments are summarized in Tables 5 and 6, wherein "DBTA" refers to dibenzoyltartaric acid.

TABLE 5

Investigation of the reaction conditions

| Batch No. | VIb | Solvent | Water | NaNO$_2$ | 50% H$_2$SO$_4$ | Reaction Temp. | Before the addition of NaNO$_2$ | After the reaction completes |
|---|---|---|---|---|---|---|---|---|
| T5-1 | 1.0 X VIb (Mother liquor) | 40 mL Acetone (20 V) | 2 mL (1 V) | 0.2 g 1.5 eq. | | 20° C. | Clear solution after the addition of water | Much solid (DBTA) precipitated out, and the mixture still can be stirred. |
| T5-2 | | 28 mL Acetone (14 V) | 2 mL (2 V) | | | 20° C. | | Much solid (DBTA) precipitated out, and the mixture was difficult to stir. |
| T5-3 | | 14 mL Acetone (7 V) | 2 mL (1 V) | | | 20° C. | | Much solid (DBTA) precipitated out, and the mixture still can be stirred. (Similar to the 1$^{st}$ reaction) |
| T5-4 | | 14 mL Acetone (7 V) | 2 mL (1 V) | | | 40° C. | | Much solid (DBTA) precipitated out, and the mixture still can be stirred. (Similar to the 1$^{st}$ reaction) |
| T5-5 | | 14 mL Acetone (7 V) | 4 mL (2 V) | | | 20° C. | | Clear solution |
| T5-6 | | 10 mL MeCN (5 V) | 4 mL (2 V) | | 2.0 eq. | 20° C. | Clear solution after stirring for 0.5 h | Clear solution |

All six experiments were conducted using the mother liquor (VIb) obtained from large scale manufacturing. The mother liquor was concentrated, and then water was charged into the reaction mixture. The behavior of the reactions was observed and noted in Table 5. Next, sodium nitrite and sulfuric acid (if needed) were added into the reaction mixture, and the reactions were monitored by HPLC.

In Experiment T5-1, the volume of the reaction mixture was close to the full capacity of the reactor. The reaction mixture was a clear solution after the addition of water. However, a large amount of solid precipitated out during the reaction. The reaction mixture could still be stirred after the completion of the reaction, but some solid clung to the inner wall of the reactor.

In order to increase the reactor capacity, the next two experiment employed a smaller volumes of solvent. In Experiment T5-2, 14 volumes of acetone were used. In Experiment T5-3, 7 volumes of acetone were used. A large amount of solid precipitated out in both experiments. Particularly in Experiment T5-2, which used 14 volumes of solvent, the reaction mixture exhibited a much worse stirring behavior. The experiments indicate that water is helpful in dissolving DBTA.

Experiment T5-4 was an attempt to improve the stirring behavior by increasing the reaction temperature to 40° C. However, it did not achieve the desired result.

In Experiment T5-5, 2 volumes of water were used. The reaction mixture was still a clear solution even after the completion of the reaction, which could make the process robust.

In Experiment T5-6, the reaction solvent was switched to acetonitrile with two volumes of water. However, the reaction mixture required stirring for about half an hour to reach a clear solution. The reaction mixture was also a clear solution when the reaction was complete.

The in-process control data of the six experiments are shown in Table 6.

TABLE 6

Investigation of the reaction conditions

| | Materials | | | Solution after | IPC (IV/II) %* | |
|---|---|---|---|---|---|---|
| Batch No. | Solvent | Water | Reaction Temp. | concentration or solvent switch | 2 h | 18 h |
| T5-1 | 40 mL Acetone (20 V) | 2 mL (1 V) | 20° C. | 72.07/11.39 | 17.69/65.29 | 2.49/79.35 |
| T5-2 | 28 mL Acetone (14 V) | 2 mL (1 V) | 20° C. | 73.21/10.94 | 31.63/52.19 | 2.59/78.78 |
| T5-3 | 14 mL Acetone (7 V) | 2 mL (1 V) | 20° C. | 72.60/11.12 | 10.83/70.68 | 2.29/79.64 |
| T5-4 | 14 mL Acetone (7 V) | 2 mL (1 V) | 40° C. | 72.14/11.23 | 4.06/77.49 | 2.00/75.26 |
| T5-5 | 14 mL Acetone (7 V) | 4 mL (2 V) | 20° C. | 71.15/11.77 | 6.73/76.18 | 1.65/81.70 |
| T5-6 | 10 mL MeCN (5 V) | 4 mL (2 V) | 20° C. | 71.50/11.64 | 1.40/82.40 | 1.22/82.32 |

*Determined by peak area integration of HPLC graph.

Several observations can be made from the experimental results in Table 6. First, the reactions at 20° C. affords similar results after stirring for 18 hours, but raising the reaction temperature to 40° C. leads to a lower product purity. Second, using a smaller volume of solvent (and thus a high concentration of reactants) resulted in a higher reaction rate. For example, only about 7% of salt (VIb) remained after stirring for 2 hours in Experiment T5-5. Last, using either acetone or acetonitrile as the solvent gives similar results.

Example B4

Further Investigation of the Recovery Process

Three experiments were conducted on 20 gram scale to further investigate the reaction conditions. The details of the experiments are summarized in Tables 7, 8, and 9.

All three experiments were conducted using the mother liquor (VIb) obtained from large scale manufacturing. The mother liquor was concentrated, and then water was charged into the reaction mixture. The behavior of the reactions was observed and noted in Table 7. Next, sodium nitrite and sulfuric acid (if needed) were added into the reaction mixture, and the reactions were monitored by HPLC.

In Experiment T7-1, the reaction was conducted using the mother liquor directly without concentration. The reaction mixture was a clear solution after the addition of water. However, a large amount of solid precipitated out during the reaction which rendered the reaction mixture difficult to stir.

In Experiment T7-2, a solvent switch was first carried out to obtain a solution in acetonitrile. The reaction mixture was initially a sticky solution but became a clear solution after adding water and stirring for half an hour. No solids of DBTA precipitated out during the course of reaction, and the reaction mixture stayed clear.

TABLE 7

Investigation of the reaction conditions

| | | Materials | | | | | Observation during the reaction | |
|---|---|---|---|---|---|---|---|---|
| Batch No. | VIb | Solvent | Water | NaNO$_2$ | 50% H$_2$SO$_4$ | Reaction Temp. | Before the addition of NaNO$_2$ | After the reaction complete |
| T7-1 | 1.0 X VIb (Mother liquor) | 249 mL Acetone (12.5 V, without concentration) | 20 mL (1 V) | 2.44 g 1.8 eq. | | 20° C. | Clear solution after the addition of water. | Much solid (DBTA) precipitated out, and the mixture was difficult to stir. |
| T7-2 | | 100 mL MeCN (5 V) | 40 mL (2 V) | | 2.0 eq. | | Clear solution after stirring for 0.5 h. | No solid (DBTA) precipitated out. The mixture was clear. |
| T7-3 | | 120 mL Acetone (6 V) | 40 mL (2 V) | | | | Clear solution after the addition of water. | No solid (DBTA) precipitated out. The mixture was clear. |

In Experiment T7-3, the reaction was concentrated to 6 volumes. The reaction mixture became a clear solution after the addition of water. No solids of DBTA precipitated out during the course of the reaction, and the reaction mixture was also a clear solution when the reaction was complete.

The in-process control results of these three experiments are summarized in Table 8.

TABLE 8

Investigation of the reaction conditions

| Batch No. | Materials | | Initial purity | Solution after concentration or solvent switch | IPC (IV/II) %* | |
|---|---|---|---|---|---|---|
| | Solvent | Water | | | 2 h | 18 h |
| T7-1 | 249 mL Acetone (12.5 V, without concentration) | 20 mL (1 V) | 78.19/7.13 | | 7.65/77.51 | 0.48/82.72 |
| T7-2 | 100 mL MeCN (5 V) | 40 mL (2 V) | | 77.46/7.50 | 0.75/85.10 | 0.34/85.21 |
| T7-3 | 120 mL Acetone (6 V) | 40 mL (2 V) | | 77.00/8.22 | 1.15/83.71 | 0.86/83.04 |

*Determined by peak area integration of HPLC graph.

The purity of alcohol (II) obtained from the three experiments was almost the same. Chiral HPLC confirmed that all three experiments produced alcohol (II) as a racemic mixture. However, the reaction without concentration (Experiment T7-1) required a longer period of time to convert all the starting material to the product.

Using lower volumes of solvent (and thus higher concentrations) resulted in higher reaction rate in Experiments T7-2/3. There was only about 1% of the starting material (VIb) remaining after stirring for 2 hours.

All three experiments were further continued with work-up and crystallization procedures. In Experiments T7-1/2, the reaction mixture was diluted with 100 mL isopropyl acetate and 100 mL water, then treated with 10% aqueous sodium hydroxide to adjust the mixture's pH to about 10. In Experiment T7-3, the reaction mixture was diluted with 100 mL isopropyl acetate, then treated with about 80 mL of 10% aqueous sodium hydroxide to adjust the mixture's pH to about 10. In order to achieve high recovery, the aqueous layer was back-extracted with 100 mL isopropyl acetate. The combined organic layer was used to crystallize salt (IIa), by first switching solvent to 10 volumes of acetone and then acidified with 1.5 equivalents of 37% HCl.

The final results for the dry cakes of salt (IIa) are shown in Table 9. RT stands for HPLC retention time. The major impurity at RT 7.5 min is identified and fully characterized. The chemical structure is assigned as VII in Table 9.

TABLE 9

Results from crystallization studies

| Expt. # | | | T7-1 | T7-2 | T7-3 |
|---|---|---|---|---|---|
| RT 5.4 min | Mesityl oxide | 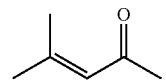 | 0.02 | 0.02 | 0.33 |
| RT 6.7 min | (V) | 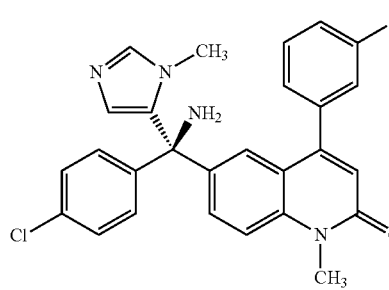 | 0.30 | 0.11 | 0.10 |

TABLE 9-continued

Results from crystallization studies

| Expt. # | | T7-1 | T7-2 | T7-3 |
|---|---|---|---|---|
| RT 7.5 min (VII) | [structure: 4-nitrophenyl analog with OH] | 0.15 | 1.12 | 0.90 |
| RT 8.1 min (II) | [structure: 4-chlorophenyl analog with OH] | 98.93 | 97.77 | 97.75 |
| RT 8.5 min | [structure: 4-chlorophenyl analog without OH] | 0.04 | 0.10 | 0.13 |
| RT 9.0 min | [structure: 4-chlorophenyl analog with OMe] | 0.06 | 0.18 | 0.28 |
| RT 9.2 min | | 0.02 | 0.08 | 0.11 |
| RT 11.3 min | | 0.09 | 0.12 | 0.08 |
| RT 11.5 min | | 0.20 | 0.17 | 0.10 |

TABLE 9-continued

Results from crystallization studies

| Expt. # | | T7-1 | T7-2 | T7-3 |
|---|---|---|---|---|
| RT 11.9 min | (I) 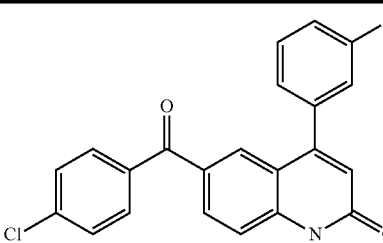 | 0.10 | 0.16 | 0.23 |

After crystallization with acetone, the purity of alcohol (IIa) is almost 98% in the final product.

Example B5

Investigation of Impurity (VII)

Eight experiments were conducted to study the formation of impurity (VII). The details of these experiments are summarized in Table 10.

impurity. However, it should be noted that while a low volume of water can afford better results in term of the purity profile, but at the same time the low volume of water may causes mixing problems. This is the case in Experiment T10-1, where the reaction mixture was almost not stirrable since it had no water in the reaction mixture.

Experiment T10-5 (6 volumes of acetone solution with 0.5 volume of water) resulted in only 0.17% of impurity (VII) in a 3 gram scale reaction. In order to further verify the

TABLE 10

Investigation of impurity (VII)

| | | | | | Observation during the reaction | |
|---|---|---|---|---|---|---|
| Batch No. | Materials | | | IPC for 18 h Impurity | Before the addition of | After the reaction |
| | VIb | Acetone | Water | VII | NaNO₂ | complete |
| T10-1 | 1.0 X VIb (Mother liquor) | 12.5 V (Without concentration) | 0 V | 0.12% | Clear solution | Much solid (DBTA) precipitated out, and the mixture was not able to stir. |
| T10-2 | | | 0.5 V | 0.15% | | Much solid (DBTA) precipitated out, and the mixture was difficult to stir. |
| T10-3 | | | 1 V | 0.30% | | Much solid (DBTA) precipitated out, and the mixture still can be stirred. |
| T10-4 | | | 2 V | 0.52% | | No solid (DBTA) precipitated out. The mixture was clear. |
| T10-5 | | 6 V | 0.5 V | 0.17% | | Much solid (DBTA) precipitated out, and the mixture still can be stirred. |
| T10-6 | | | 1 V | 0.40% | | Much solid (DBTA) precipitated out, and the mixture was difficult to stir. |
| T10-7 | | | 2 V | 0.61% | | No solid (DBTA) precipitated out. The mixture was clear. |
| T10-8 | | | 6 V | 1.04% | Much solid (B) precipitated out | Much solid (DBTA) precipitated out, and the mixture still can be stirred. |

The experimental data in Table 10 indicate that more water in the reaction mixture leads to a higher content of impurity (VII). This is especially the case in Experiment T10-8, where 6 volumes of water resulted in 1.04% of the process, the same procedure in Experiment T10-5 was repeated on larger scales in three further experiments. The details of the three experiments are summarized in Tables 11 and 12.

TABLE 11

Further investigation of the recovery process

| Batch No. | VIb[†] | Materials Acetone | Water | NaNO$_2$ | Reaction Temp. | Observation during the reaction Before the addition of NaNO$_2$ | After the reaction complete |
|---|---|---|---|---|---|---|---|
| T11-1 | 20 g | 6 V (Concentrate the solution to 6 V) | 0.5 V | 1.8 eq. | 20° C. | Clear solution | Much solid (DBTA) precipitated out, and the mixture still can be stirred. |
| T11-2 | 40 g | | | | | | Much solid (DBTA) precipitated out. The upper reaction mixture was too viscous to stir, and it was almost jelly. |
| T11-3 | 100 g | | | | | | |

[†]Calculated mass of salt (VIb) contained in mother liquor.

TABLE 12

Further investigation of the recovery process

| Expt. # | | | T11-1 | T11-2 | T11-3 |
|---|---|---|---|---|---|
| RT 5.4 min | Mesityl oxide | | 0.07 | 0.05 | 0.02 |
| RT 6.7 min | (V) | | N.D. | 0.16 | 0.02 |
| RT 7.5 min | (VII) | | 0.18 | 0.44 | 0.43 |
| RT 8.1 min | (II) | | 98.20 | 97.47 | 98.33 |

TABLE 12-continued

Further investigation of the recovery process

| Expt. # | | T11-1 | T11-2 | T11-3 |
|---|---|---|---|---|
| RT 8.5 min | [structure: 1-methylimidazole-CH(4-chlorophenyl)- attached to 4-(3-chlorophenyl)-1-methylquinolin-2(1H)-one] | 0.15 | 0.19 | 0.15 |
| RT 9.0 min | [structure: 1-methylimidazole-C(OMe)(4-chlorophenyl)- attached to 4-(3-chlorophenyl)-1-methylquinolin-2(1H)-one] | 0.33 | 0.37 | 0.17 |
| RT 9.2 min | | 0.10 | 0.16 | 0.06 |
| RT 11.3 min | | 0.16 | 0.24 | 0.12 |
| RT 11.5 min | | 0.24 | 0.27 | 0.05 |
| RT 11.9 min (I) | [structure: (4-chlorophenyl)(4-(3-chlorophenyl)-1-methyl-2-oxo-1,2-dihydroquinolin-6-yl)methanone] | N.D. | 0.25 | 0.16 |

In the experiment on 20 g scale (Experiment T11-1), although much solid (DBTA) precipitated out at the completion of the reaction, the reaction mixture could still be stirred. However, when this process was magnified to the scales of 40 g or 100 g, the process experienced mixing problems. The reaction mixture was too viscous to stir at the completion of the reaction. This is especially so in the upper portion of the reaction mixture, where it was almost jelly-like.

Furthermore, the content of impurity (VII) was also higher than usual (about 0.2%) in the scaled up reactions.

In an attempt to further optimize the process, yet another three experiments were conducted with different amounts of acetone and water on a 60 gram scale. The details of these experiments are summarized in Table 13.

TABLE 13

Further investigation of the recovery process

| Batch No. | Materials | | | Observation during the reaction (VIb/VII/II)* | | | |
|---|---|---|---|---|---|---|---|
| | VIb† | Acetone | Water | IPC for 2 h | | IPC for 18 h | |
| T13-1 | 60 g | 9 V | 0.75 V | Clear solution | 3.66/0.20/86.47 | Much solid (DBTA) precipitated out. The | 0.14/0.27/90.17 |
| T13-2 | | 6 V | 1 V | Clear solution | 0.13/0.55/89.04 | upper reaction mixture was too viscous to stir, and it was almost jelly. | 0.13/0.58/89.26 |

TABLE 13-continued

Further investigation of the recovery process

| Batch | Materials | | | Observation during the reaction (VIb/VII/II)* | | |
|---|---|---|---|---|---|---|
| No. | VIb† | Acetone | Water | IPC for 2 h | IPC for 18 h | |
| T13-3 | | 6 V | 1.5 V | Clear solution | 0.03/0.82/89.22 | Clear solution 0.10/0.77/90.28 |

*Determined by peak area integration of HPLC graph.
†Calculated mass of salt (VIb) contained in mother liquor.

The results in Table 13 indicate that the reactions with low volumes of water (0.75 and 1 volume) has mixing problems, especially after stirring for long hours. The reaction with 1.5 volumes of water always gives a clear solution even after the completion of reaction, but it resulted in a higher level of impurity.

Two experiments were conducted with procedure in T13-1 at different temperatures (30 and 40° C.). The details of these experiments are summarized in Table 14.

TABLE 14

Further study of the recovery process

| Batch | Materials | | | | Observation during the reaction (VIb/VII/II)* | | |
|---|---|---|---|---|---|---|---|
| No. | VIb† | Acetone | Water | Temp. | IPC for 1 h | IPC for 18 h | Work-up |
| T14-1 | 60 g | 9 V | | 30° C. | Clear solution 2.47/0.18/87.78 | Much solid (DBTA) precipitated out. The | 0.11/0.51/87.91 |
| T14-2 | | | 0.75 V | 40° C. | Clear solution 0.13/1.13/89.47 | upper reaction mixture was too viscous to stir, and it was almost jelly. | 0.09/0.38/88.38 |

*Determined by peak area integration of HPLC graph.
†Calculated mass of salt (VIb) contained in mother liquor.

As the experimental results in Table 14 demonstrate, the reactions at high temperatures (30° C. and 40° C.) still experience mixing problems, especially after stirring for long hours. Moreover, the content of impurity (VII) were also higher than at 20° C. (20° C., RT 7.5 min about 0.2%).

It is determined from the experimental results here that using 6 volumes of acetone and 1.5 volumes of water minimizes the mixing problems and provides the optimal results in the final recovery process.

Example B6

Demo Batch in Kilo Lab

A demo batch of the mother liquor recovery process was conducted on 1.445 kg scale in a kilo lab with a 30-liter reactor. The details of the demo batch are summarized in Tables 15 and 16. In this experiment, multiple batches of the mother liquor from large scale manufacturing were combined, and their total volume was about 20 liters.

The mother liquor was concentrated to 6 volumes, and 1.5 volumes of water were added. Next, 1.8 equivalents of sodium nitrite were charged into the reactor slowly while maintaining the reaction mixture at a temperature below 40° C. At the completion of the reaction, 5 volumes of isopropyl acetate were added, and 10% aqueous solution of sodium hydroxide was charged to adjust the mixture to pH 10. Then the aqueous layer after phase cut was re-extracted with 5 volumes of isopropyl acetate. Finally, 1.5 equivalents of concentrated hydrochloric acid were charged into the reaction mixture to crystallize the product after solvent switch.

TABLE 15

Demo batch in kilo lab

| | Materials | | | | | | Work-up | | |
|---|---|---|---|---|---|---|---|---|---|
| Batch | Reaction | | | | | | | 10% | Crystallization |
| No. | VIb† | Acetone | Water | NaNO$_2$ | Temp. | | $^i$PrAc | NaOH | Conc. HCl |
| T15 | 1.445 kg | The mother liquor was concentrated to 6 V | 1.5 V 2.16 L | 1.8 eq. 175 g | 20° C. | | 10 V 14.44 L | 9 L pH = 10 | 1.5 eq. 208.4 g |

†Total mass of salt (VIa) and (VIb) contained in mother liquor.

TABLE 16

| | | Results from demo batch in kilo lab | | | | | |
|---|---|---|---|---|---|---|---|
| Expt. # | | | T15 | | | | |
| | | Chart | Mother liquor before reaction | IPC | Solution before crystallization | Mother liquor | Dry cake |
| RT 5.4 min | Mesityl oxide | *(structure)* | 0.96 | 0.25 | 0.11 | 30.86 | 0.05 |
| RT 6.7 min | (V) | *(structure)* | 74.79 | 0.15 | 0.05 | 0.11 | 0.05 |
| RT 7 4 min | DBTA | | — | — | 0.09 | 0.23 | N.D. |
| RT 7.5 min | (VII) | *(structure)* | N.D. | 0.61 | 0.99 | 0.55 | 0.73 |
| RT 8.1 min | (II) | *(structure)* | 16.55 | 90.72 | 94.18 | 29.25 | 97.10 |
| RT 8.5 min | | *(structure)* | 0.24 | 0.36 | 0.21 | 1.09 | 0.24 |

TABLE 16-continued

Results from demo batch in kilo lab

| | | | | | | |
|---|---|---|---|---|---|---|
| RT 9.0 min | 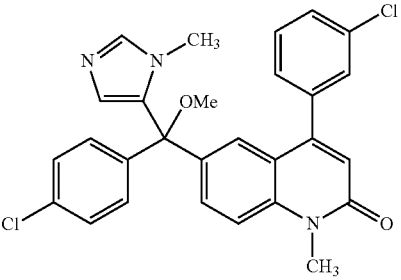 [SMILES: COC(c1ccc(Cl)cc1)(c1ccc2c(c1)c(-c1cccc(Cl)c1)cc(=O)n2C)c1cncn1C] | 2.71 | 2.58 | 1.12 | 12.75 | 0.43 |
| RT 9.2 min | | 0.85 | 0.87 | 0.40 | 4.47 | 0.17 |
| RT 11.3 min | | 0.11 | 0.35 | 0.19 | 0.68 | 0.24 |
| RT 11.5 min | | 0.01 | 0.39 | 0.36 | 0.78 | 0.28 |
| RT 11.9 min (I) | 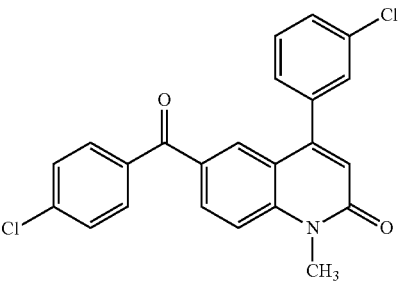 [SMILES: Cn1c(=O)cc(-c2cccc(Cl)c2)c2cc(C(=O)c3ccc(Cl)cc3)ccc21] | 0.61 | 0.87 | 0.72 | 5.70 | 0.26 |
| Yield or Yield loss | | | | | 5% | 97% |

In this experiment, the reaction mixture was a clear solution even after stirring overnight. The entire process showed good behavior at the various stages of the demo batch, including reaction, work-up and crystallization. In the final isolated product, the purity of salt (IIa) was 97.10%, and the content of impurity (VII) was 0.73%. Furthermore, the product salt (IIa) isolated after this recycling process is racemic.

The yield loss from crystallization was 5%, and the yield for the overall recovery process was 97%, based on the amount of (S)-(−) tipifarnib in the mother liquor (VIb).

Example C1

Recycling Process without Sodium Nitrite

Four experiments were carried out with various solvents at elevated temperatures in order to further study the recovery process without using sodium nitrite. These experiments are detailed in Tables 17 and 18. All the experiments used the dry solid of salt (VIa). The behavior of the reactions were observed and recorded after adding solvent, after adding water, and after stirring the reaction mixture for 48 hours.

TABLE 17

Investigation of reaction solvent: reaction set up.

| | Materials | | | Observation | | |
|---|---|---|---|---|---|---|
| Batch No. | VIa | H$_2$O 1.0 V | Solvent 6.0 V | After adding solvent | After adding water | After stirring for 48 h |
| T17-1 | 1.0 g 1.0 X Solid | 1 mL | 6 mL MeCN | Undissolved | Some solid precipitated out (RT) | Some solid precipitated out |
| T17-2 | | | 6 ml MEK | Undissolved | Some solid precipitated out (RT) | Some solid precipitated out |
| T17-3 | | | 6 ml Acetone | Undissolved | Some solid precipitated out (RT) | Some solid precipitated out |
| T17-4 | | | 6 ml DMF | Dissolved | Clear solution | Clear solution |

TABLE 18

Investigation of reaction solvent: experimental results.

| Batch No. Temperature (Solvent) | Stirring Time | Results | | | | | Enantiomeric Composition of II |
|---|---|---|---|---|---|---|---|
| | | RT = 1.26 min | Benzoic Acid | IV | DBTA | II | |
| S.M. VIa | | N.D. | N.D. | 64.89 | 34.07 | 1.04 | |
| T17-1 | 3 h | 3.46 | 4.97 | 14.77 | 17.45 | 55.62 | |
| 80° C. | 6 h | 4.12 | 7.70 | 7.70 | 10.19 | 64.96 | |
| (MeCN/H$_2$O) | 24 h | N.D. | 15.45 | 4.91 | 0.74 | 75.21 | |
| | 48 h | 1.78 | 16.26 | 4.01 | 0.41 | 70.64 | 48.69/51.31 |
| T17-2 | 3 h | 3.88 | 4.58 | 37.04 | 20.73 | 32.49 | |
| 80° C. | 6 h | 5.58 | 7.80 | 22.43 | 12.89 | 47.06 | |
| (MEK/H$_2$O) | 24 h | 4.95 | 16.80 | 2.04 | 0.98 | 69.67 | 48.09/51.91 |
| T17-3 | 3 h | 2.40 | 2.47 | 44.43 | 25.65 | 22.41 | |
| reflux at 60° C. | 6 h | 4.17 | 4.34 | 36.63 | 22.25 | 31.33 | |
| (acetone/H$_2$O) | 24 h | 5.90 | 10.10 | 11.50 | 7.99 | 59.67 | |
| | 48 h | 4.52 | 13.86 | 4.98 | 2.39 | 67.48 | 47.87/52.13 |
| T17-4 | 3 h | 3.16 | 4.50 | 39.54 | 19.24 | 27.59 | |
| 80° C. | 6 h | 3.87 | 7.00 | 29.91 | 12.18 | 37.92 | |
| (DMF/H$_2$O) | 24 h | 3.13 | 13.39 | 11.87 | 1.32 | 58.44 | |
| | 48 h | 1.01 | 17.12 | 5.01 | 0.11 | 65.11 | 48.38/51.62 |

In experiment T17-1 where MeCN was used as the reaction solvent, only 7.70% of unconverted amine (IV) remained after stirring for 6 hours at 80° C. However, the reaction of reaction became slower subsequently, with 4.01% of unconverted amine (IV) still remaining after stirring for 24 hours. In experiment T17-2 where methylethylketone (MEK) was used as the reaction solvent, 22.43% of unconverted amine (IV) remained after stirring for 6 hours at 80° C. The amount of unconverted amine (IV) decreased further to about 2% after stirring for 24 hours. In experiment T17-4 where DMF was used the reaction solvent, the experiment did not afford better results than the other experiments that used different solvents.

The enantiomeric composition of alcohol (II) in the product solution was tested, and it was racemic within the error of measurement.

Example C2

Investigation of the Volume of Water

Six further experiments were carried out to investigate the impact of different volumes of water. These experiments are detailed in Tables 19 and 20. All the experiments used the dry solid of salt (VIa). The behavior of the reactions were observed and recorded after adding solvent, after adding different volumes of water, and after stirring the reaction mixture for 48 hours.

TABLE 19

Investigation of the volume of water: reaction set up.

| Batch No. | Materials | | | Observation | | |
|---|---|---|---|---|---|---|
| | VIa | H$_2$O | Solvent | After adding solvent | After adding water | After stirring for 48 h at 80° C. |
| T19-1 | 1.0 g 1.0 X Solid | 1 mL | 6 mL MeCN | Undissolved | Some solid precipitated out (RT) | Some solid precipitated out |
| T19-2 | | 2 mL | | Undissolved | Some solid precipitated out (RT) | Some solid precipitated out |
| T19-3 | | 3 mL | | Undissolved | Some solid precipitated out (RT) | Clear solution |
| T19-4 | | 1 mL | 6 mL MEK | Undissolved | Some solid precipitated out (RT) | Some solid precipitated out |
| T19-5 | | 2 mL | | Undissolved | Some solid precipitated out (RT) | Clear solution with two phase |
| T19-6 | | 3 mL | | Undissolved | Some solid precipitated out (RT) | Clear solution with two phase |

TABLE 20

Investigation of the volume of water: experimental results.

| Batch No. | Stirring Time | RT = 1.26 min | Benzoic Acid | IV | DBTA | II | IV/(IV + II) |
|---|---|---|---|---|---|---|---|
| S.M. VIa | | N.D. | N.D. | 64.89 | 34.07 | 1.04 | 98.4 |
| T19-1 | 3 h | 3.46 | 4.97 | 14.77 | 17.45 | 55.62 | 21.0 |
| (MeCN/H$_2$O = | 6 h | 4.12 | 7.70 | 7.70 | 10.19 | 64.96 | 10.6 |
| 6 V/1 V) | 24 h | N.D. | 15.45 | 4.91 | 0.74 | 75.21 | 6.1 |
| | 48 h | 1.78 | 16.26 | 4.01 | 0.41 | 70.64 | 5.4 |
| T19-2 | 3 h | 3.34 | 4.06 | 10.36 | 21.34 | 58.46 | 15.1 |
| (MeCN/H$_2$O = | 6 h | 4.27 | 5.86 | 5.85 | 16.34 | 64.57 | 8.3 |
| 6 V/2 V) | 24 h | 4.90 | 12.33 | 3.79 | 3.85 | 70.69 | 5.1 |
| | 48 h | 4.11 | 15.08 | 3.56 | 1.07 | 71.61 | 4.7 |
| T19-3 | 3 h | 3.22 | 3.23 | 7.03 | 24.51 | 59.86 | 10.5 |
| (MeCN/H$_2$O = | 6 h | 4.23 | 4.65 | 3.64 | 20.48 | 64.50 | 5.3 |
| 6 V/3 V) | 24 h | 6.76 | 9.65 | 2.42 | 8.89 | 68.90 | 3.4 |
| | 48 h | 6.90 | 12.070 | 2.42 | 3.85 | 70.61 | 3.3 |
| T19-4 | 3 h | 3.88 | 4.58 | 37.04 | 20.73 | 32.49 | 53.3 |
| (MEK/H$_2$O = | 6 h | 5.58 | 7.80 | 22.43 | 12.89 | 47.06 | 32.3 |
| 6 V/1 V) | 24 h | 4.95 | 16.80 | 2.04 | 0.98 | 69.67 | 2.8 |
| T19-5 | 3 h | 3.30 | 4.44 | 34.72 | 21.48 | 34.51 | 50.2 |
| (MEK/H$_2$O = | 6 h | 4.42 | 6.78 | 24.64 | 16.17 | 46.13 | 34.8 |
| 6 V/2 V) | 24 h | 6.62 | 15.50 | 2.62 | 2.68 | 70.86 | 3.6 |
| | 48 h | 5.19 | 18.68 | 1.16 | 0.74 | 72.54 | 1.6 |
| T19-6 | 3 h | 2.64 | 4.14 | 35.16 | 22.30 | 34.48 | 50.5 |
| (MEK/H$_2$O = | 6 h | 3.80 | 6.83 | 22.62 | 16.57 | 48.62 | 31.8 |
| 6 V/3 V) | 24 h | 8.48 | 13.08 | 4.61 | 5.29 | 67.60 | 6.4 |
| | 48 h | 6.67 | 17.79 | 0.95 | 1.35 | 72.28 | 1.3 |

It can be concluded from the experimental results in Tables 19 and 20 that increasing the amount of water from 1.0 to 3.0 volumes moderately increased the reaction rate, because the increased amount of water could solubilize any solid precipitated during the reaction. However, there was nonetheless approximately 3% to 6% of unconverted amine (IV) after stirring for 24 hours.

It can also be concluded from the experimental results in Tables 19 and 20 that MeCN appeared to be a superior solvent than MEK, especially when looking at the results at 6 h.

Example C3

Investigation of Acid Additives

Four further experiments were carried out to investigate the accelerating effect of an acid additive, 5 wt % sulfuric acid, on the rate of reaction. The experiments were conducted using the mother liquor (VIb) with the same solvent/water ratio (6.0 V to 3.0 V) at 80° C. The experiments are summarized in Tables 21 and 22.

TABLE 21

Investigation of acid additive: reaction set up.

| | Materials | | | | Observation | | | |
|---|---|---|---|---|---|---|---|---|
| Batch No. | VIb† 1.0 X (mother liquor) | H$_2$O | Solvent 6.0 V | Additive | After adding solvent | After adding water | After heating to 80° C. | After stirring for 24 h at 80° C. |
| T21-1 | 45 g | 3.0 V | MeCN | None | Undissolved | Undissolved | Clear solution | Clear solution (RT) |
| T21-2 | 5 g | | | 5% H$_2$SO$_4$ | | | | |
| T21-3 | 45 g | | MEK | None | Undissolved | Undissolved | Clear solution | Clear solution with two phase |
| T21-4 | 5 g | | | 5% H$_2$SO$_4$ | | | | |

†Calculated mass of salt (VIb) contained in mother liquor.

TABLE 22

Investigation of acid additive: experimental results.

| Batch No. | Stirring Time | RT = 1.26 min | Benzoic Acid | IV | DBTA | II | IV/(IV + II) |
|---|---|---|---|---|---|---|---|
| S.M. VIb (Mother liquor) | | 0.16 | 0.24 | 61.04 | 35.86 | 0.41 | 99.3 |

TABLE 22-continued

Investigation of acid additive: experimental results.

| Batch No. | Stirring Time | RT = 1.26 min | Benzoic Acid | IV | DBTA | II | IV/(IV + II) |
|---|---|---|---|---|---|---|---|
| T21-1 (MeCN) | 2 h | 3.98 | 3.05 | 1.95 | 53.05 | 36.07 | 5.1 |
| | 4 h | 7.05 | 5.87 | 0.13 | 45.13 | 38.88 | 0.3 |
| | 6 h | 10.26 | 9.40 | N.D. | 36.80 | 39.48 | N.D. |
| | 8 h | 10.65 | 9.88 | N.D. | 35.84 | 39.47 | N.D. |
| T21-2 (5% $H_2SO_4$ in MeCN) | 2 h | 3.05 | 2.21 | 1.47 | 55.72 | 36.13 | 3.9 |
| | 4 h | 5.42 | 4.04 | 0.11 | 50.65 | 37.98 | 0.3 |
| | 6 h | 8.48 | 6.64 | N.D. | 43.41 | 39.29 | N.D. |
| | 8 h | 8.57 | 6.78 | N.D. | 43.68 | 38.68 | N.D. |
| T21-3 (MEK) | 2 h | 3.31 | 2.26 | 13.94 | 54.89 | 24.32 | 36.4 |
| | 4 h | 5.93 | 4.31 | 5.68 | 49.18 | 33.17 | 14.6 |
| | 6 h | 9.05 | 7.16 | 1.67 | 41.58 | 38.16 | 4.2 |
| | 8 h | 9.45 | 7.55 | 1.24 | 41.57 | 38.12 | 3.2 |
| | 16 h | 12.88 | 12.83 | 0.05 | 30.68 | 40.49 | 0.1 |
| T21-4 (5% $H_2SO_4$ in MEK) | 2 h | 2.96 | 1.75 | 12.19 | 55.37 | 26.56 | 31.5 |
| | 4 h | 13.33 | 4.18 | 6.21 | 42.10 | 32.94 | 15.9 |
| | 6 h | 8.54 | 5.48 | 1.04 | 46.00 | 37.44 | 2.7 |
| | 8 h | 7.67 | 5.66 | 0.84 | 46.58 | 37.99 | 2.2 |

When using the mother liquor (VIb) directly in the racemization reaction, the rate of reaction was much faster when using MeCN as the solvent than MEK. Almost all of the starting material (IV) converted to alcohol (II) within four hours in MeCN, while it took approximately 16 hours under analogous conditions in MEK.

The acid additive (5 wt % sulfuric acid) appeared to have limited accelerating effect on the rate of reaction. Experimental results in the presence and absence of the acid additive are largely similar.

Example C4

Manufacture Procedure

The transformation from the mother liquor (VIb) to alcohol hydrochloride (IIa) may be effected in the following procedure:

1. Charge a reactor with mother liquor (VIb) containing 1.64 kg (1.6 mol) of salts (VIa) and (VIb).
2. Concentrate to 5 L (3.0 V), then charge 7.3 kg (4.5 X) of methylethylketone and 4.5 kg (2.7 X) of process water.
3. Stir the resulting biphasic mixture at 76° C. for 14 hours.
4. Monitor the reaction by UPLC until the ratio IV/(IV+II) is equal to or less than 2%.
5. Add 3.8 kg (2.3 X) process water.
6. Add 2.4 kg of 30 w/w % NaOH solution such that the reaction mixture has pH ≥8.
7. Separate layers.
8. Extract the aqueous layer with IPAc (6.0 kg, 3.7 X).
9. Add 4.5 kg (2.7 X) process water to the combined organic layers.
10. Age the resulting mixture at 20° C. for 12 hours.
11. Concentrate the mixture at 50° C. under reduced pressure until its volume is approximately 9 L (5.5 V).
12. Add 3.3 kg (2.0 X) IPAc.
13. Age the resulting slurry at 20° C. for 12 hours.
14. Filter the slurry and rinse the wet cake with 1.3 kg (0.8 X) of acetone.
15. Charge the wet cake with acetone (4.7 X, 6 V).
16. Add 35% HCl solution (224 g, 2.1 mol, 0.14 X) at 20° C. over 5 hours and age for 14 hours.
17. Filter, rinse with acetone (3.3 kg, 2.0 X), and dry at 80° C. for 72 hours under vacuum.

The above described process has a typical yield of approximately 80-90%.

The invention claimed is:

1. A method for preparing a desired enantiomer of tipifarnib comprising the steps of:
   (i) obtaining a starting material comprising tipifarnib that is not enantiopure in the desired enantiomer;
   (ii) transforming the starting material from step (i) to a racemic mixture of tipifarnib; and
   (iii) recovering the desired enantiomer of tipifarnib from the racemic mixture of tipifarnib of step (ii);
   wherein step (ii) comprises the steps of:
   (ii)(a) reacting the starting material with sodium nitrite in a reaction solvent to give a product mixture;
   (ii)(b) recovering a racemic alcohol of Formula (II) from the product mixture of step (ii)(a); and

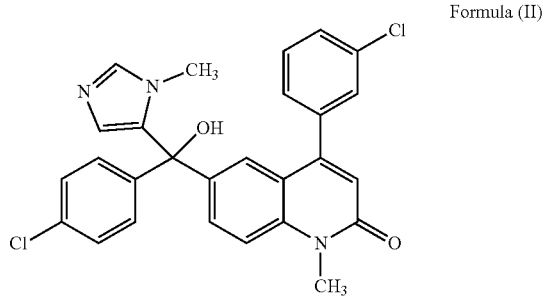 [SMILES: Cn1cncc1C(O)(c1ccc(Cl)cc1)c1ccc2c(c1)c(-c1cccc(Cl)c1)cc(=O)n2C]

Formula (II)

(ii)(c) transforming the racemic alcohol of step (ii)(b) to the racemic mixture of tipifarnib.

2. The method of claim 1, wherein the reaction solvent of step (ii)(a) is an organic solvent, water, or a mixture thereof.

3. The method of claim 2, wherein the organic solvent is miscible with water.

4. The method of claim 1, wherein step (ii)(a) takes place in the presence of an additive.

5. The method of claim 1, wherein step (ii)(b) comprises: adjusting the product mixture's pH with a base;

extracting the product mixture with an extraction solvent; and crystallizing the racemic alcohol.

6. A method for preparing a desired enantiomer of tipifarnib comprising the steps of:
(i) obtaining a starting material comprising tipifarnib that is not enantiopure in the desired enantiomer;
(ii) transforming the starting material from step (i) to a racemic mixture of tipifarnib; and
(iii) recovering the desired enantiomer of tipifarnib from the racemic mixture of tipifarnib of step (ii),
wherein step (ii) comprises the steps of:
(ii)(a) heating the starting material in a reaction solvent to give a product mixture;
(ii)(b) recovering a racemic alcohol of Formula (II) from the product mixture of step (ii)(a); and

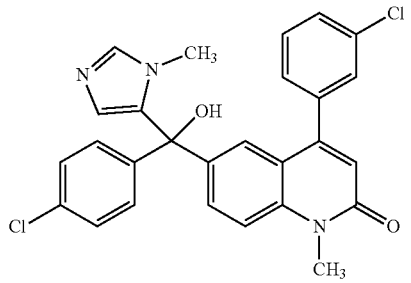

Formula (II)

(ii)(c) transforming the racemic alcohol of step (ii)(b) to the racemic mixture of tipifarnib.

7. The method of claim 6, wherein the reaction solvent of step (ii)(a) is an organic solvent, water, or a mixture thereof.

8. The method of claim 7, wherein the organic solvent is miscible with water.

9. The method of claim 6, wherein step (ii)(a) takes place in the presence of an additive.

10. The method of claim 6, wherein step (ii)(b) comprises:
adjusting the product mixture's pH with a base;
extracting the product mixture with an extraction solvent; and
crystallizing the racemic alcohol.

11. The method of claim 1, wherein step (iii) comprises:
(iii)(a) crystallizing the desired enantiomer of tipifarnib from the racemic mixture of tipifarnib in the presence of a chiral resolving agent; and
(iii)(b) separating crystals of the desired enantiomer of tipifarnib from a mother liquor.

12. The method of claim 11, wherein the method further comprises:
(iv) recycling the mother liquor of step (iii)(b) to be used as the starting material in step (i).

13. The method of claim 12, wherein the steps (i) to (iv) are run in multiple cycles.

14. The method of claim 1, wherein the desired enantiomer of tipifarnib is (R)-(+)-tipifarnib.

15. The method of claim 1, wherein the starting material of step (i) comprises an enantiomeric excess of an undesired enantiomer of tipifarnib.

16. The method of claim 6, wherein the desired enantiomer of tipifarnib is (R)-(+)-tipifarnib.

17. The method of claim 6, wherein the starting material of step (i) comprises an enantiomeric excess of an undesired enantiomer of tipifarnib.

18. The method of claim 7, wherein reaction solvent of step (ii)(a) is a mixture of an organic solvent and water.

19. The method of claim 18, wherein the organic solvent is acetonitrile, methylethylketone, acetone, DMF, or a mixture thereof.

20. The method of claim 18, wherein the organic solvent is acetone.

21. The method of claim 7, wherein step (ii)(a) takes place at a temperature ranging from about 60° C. to about 80° C.

22. The method of claim 9, wherein the additive is an acid.

23. The method of claim 22, wherein the acid is hydrochloric acid.

24. The method of claim 22, wherein the acid is sulfuric acid.

25. The method of claim 10, wherein the product mixture's pH is adjusted to about 8.

26. The method of claim 25, wherein the base is sodium hydroxide.

27. The method of claim 25, wherein the extraction solvent is isopropyl acetate.

28. The method of claim 25, wherein the racemic alcohol is crystallized as a hydrochloride salt.

29. The method of claim 11, wherein the chiral resolving agent of step (iii)(a) is (-)dibenzoyl-L-tartaric acid.

* * * * *